(12) United States Patent
Tang et al.

(10) Patent No.: US 11,965,826 B2
(45) Date of Patent: Apr. 23, 2024

(54) METHOD FOR DETERMINING HYDROGEN SULFIDE BY HEADSPACE SINGLE-DROP LIQUID PHASE MICROEXTRACTION AND INTELLIGENT DEVICE COLORIMETRY

(71) Applicant: JIANGSU UNIVERSITY OF SCIENCE AND TECHNOLOGY, Jiangsu (CN)

(72) Inventors: Sheng Tang, Jiangsu (CN); Wei Shen, Jiangsu (CN); Tong Qi, Jiangsu (CN); Mengchan Xu, Jiangsu (CN); Mengyuan Xu, Jiangsu (CN); Anni Zhu, Jiangsu (CN)

(73) Assignee: JIANGSU UNIVERSITY OF SCIENCE AND TECHNOLOGY, Jiangsu (CN)

( * ) Notice: Subject to any disclaimer, the term of this patent is extended or adjusted under 35 U.S.C. 154(b) by 469 days.

(21) Appl. No.: 17/440,189

(22) PCT Filed: Feb. 28, 2020

(86) PCT No.: PCT/CN2020/077103
§ 371 (c)(1),
(2) Date: Sep. 17, 2021

(87) PCT Pub. No.: WO2020/186995
PCT Pub. Date: Sep. 24, 2020

(65) Prior Publication Data
US 2022/0155222 A1    May 19, 2022

(30) Foreign Application Priority Data
Mar. 18, 2019  (CN) .......................... 201910201539.6

(51) Int. Cl.
*G01N 21/33*    (2006.01)
*G01N 1/22*    (2006.01)
*G01N 33/04*    (2006.01)

(52) U.S. Cl.
CPC .......... *G01N 21/33* (2013.01); *G01N 1/2214* (2013.01); *G01N 33/04* (2013.01); *G01N 2001/2217* (2013.01); *G01N 2001/2229* (2013.01)

(58) Field of Classification Search
CPC ...... G01N 21/33; G01N 1/2214; G01N 33/04; G01N 2001/2217; G01N 2001/2229; G01N 21/783; G01N 1/28
See application file for complete search history.

(56) References Cited

U.S. PATENT DOCUMENTS 3,766,634 A * 10/1973 Babcock ............... C04B 37/021
                                                         361/779
3,993,411 A * 11/1976 Babcock ............... C04B 37/021
                                                         403/404

(Continued)

FOREIGN PATENT DOCUMENTS

| CN | 105806815 | 7/2016 |
| CN | 106248633 | 12/2016 |

(Continued)

OTHER PUBLICATIONS

"International Search Report (Form PCT/ISA/210) of PCT/CN2020/077103," dated May 26, 2020, with English translation thereof, pp. 1-4.

(Continued)

*Primary Examiner* — David P Porta
*Assistant Examiner* — Gisselle M Gutierrez
(74) *Attorney, Agent, or Firm* — JCIP GLOBAL INC.

(57) ABSTRACT

The present invention provides a method for determining hydrogen sulfide ($H_2S$) by headspace single-drop liquid phase microextraction and intelligent device colorimetry, which comprises: taking a silver-gold core-shell triangular nanosheet (Ag@Au TNS) as a nanodetection probe, in combination with an analysis method of headspace single-drop microextraction (HS-SDME), specifically extracting $H_2S$ volatilized from a sample to be detected by the nano-detection probe, and detecting $H_2S$ in the extracted sample with the help of the photographing function of an intelligent device and a color picking software. Compared with the prior art, the present invention adopts intelligent device colorimetry, with the limit of detection of about 65 nM and the linear range of 0.1-100 μM, and the established method can be applied to the determination of $H_2S$ in actual samples such as egg white, milk and other opaque samples, and has the advantages of few procedures, simple operation, high detection efficiency and the like.

8 Claims, 10 Drawing Sheets

(56) References Cited

U.S. PATENT DOCUMENTS

| 2010/0133489 | A1* | 6/2010 | Mirkin | B22F 1/17 |
|---|---|---|---|---|
| | | | | 427/595 |
| 2010/0304173 | A1* | 12/2010 | Mirkin | B22F 1/056 |
| | | | | 428/570 |
| 2014/0162067 | A1* | 6/2014 | Shahjamali | C23C 18/1637 |
| | | | | 427/216 |

FOREIGN PATENT DOCUMENTS

| CN | 107607515 | | 1/2018 | | |
|---|---|---|---|---|---|
| CN | 109946249 | | 6/2019 | | |
| CN | 112138428 | A * | 12/2020 | | B01D 11/0415 |
| CN | 113640240 | A * | 11/2021 | | G01N 21/33 |
| JP | H06102181 | | 4/1994 | | |
| KR | 102051757 | | 12/2019 | | |

OTHER PUBLICATIONS

"Written Opinion of the International Searching Authority (Form PCT/ISA/237) of PCT/CN2020/077103," dated May 26, 2020, pp. 1-4.

* cited by examiner

METHOD FOR DETERMINING HYDROGEN SULFIDE BY HEADSPACE SINGLE-DROP LIQUID PHASE MICROEXTRACTION AND INTELLIGENT DEVICE COLORIMETRY

CROSS-REFERENCE TO RELATED APPLICATION

This application is a 371 of international application of PCT application serial no. PCT/CN2020/077103, filed on Feb. 28, 2020, which claims the priority benefit of China application no. 201910201539.6, filed on Mar. 18, 2019. The entirety of each of the above mentioned patent applications is hereby incorporated by reference herein and made a part of this specification.

BACKGROUND

Technical Field

The present invention belongs to the technical field of hydrogen sulfide detection, and relates to a method for determining hydrogen sulfide by headspace single-drop liquid phase microextraction and intelligent device colorimetry.

Description of Related Art

Hydrogen sulfide ($H_2S$) is a colorless acidic gas with a characteristic odor of rotten eggs. It is known that $H_2S$ can be produced in the food processing industry, coal gasification plants, and crude oil refining processes. It is the third toxic gas signal molecule following nitric oxide and carbon monoxide, and has important pathophysiological effects in many cardiovascular diseases, such as cardiac ischemia, vasodilation and neuromodulation disorder. There is increasing evidence that abnormal levels of $H_2S$ are closely associated with diabetes, Alzheimer disease and Down syndrome. When exposed to hydrogen sulfide at a concentration up to 15 ppm, a person will lose consciousness accompanied by apnea and inactivation of the olfactory system; when exposed to hydrogen sulfide at a concentration above 320 ppm, a person may die. $H_2S$ can also be produced in the deterioration process of foods such as eggs and milk. Therefore, the rapid and sensitive detection of $H_2S$ is of great significance for early warning of food deterioration or contamination events.

To date, many classical methods for determining $H_2S$ have been reported, such as gas chromatography (GC), electrochemistry and chemiluminescence. In general, the above methods are preferred automated instrumental methods for determining $H_2S$. However, those methods require moderately complex instruments and cumbersome pre-processing procedures, as well as gas (helium or nitrogen) serving as the mobile phase and reference gas mixture for analytical system calibration. In addition, the fluorescence method is widely used for the detection and real-time imaging of $H_2S$ in biological samples. In recent years, fluorescence detection methods have been widely used for the detection and real-time imaging of $H_2S$. However, the technique still has limitations such as low selectivity, low photostability, and difficulty in separating unreacted materials in practical use.

In recent years, an increasing number of studies have focused on the detection of $H_2S$ in gas phase and biological systems using nanomaterials, including carbon nanostructures, metal nanoparticles, metal oxide nanoparticles, and quantum dots. Those materials feature high selectivity as microsensors for real-time applications, and also have other outstanding advantages. For example, silver/gold nanomaterials have been reported to detect $H_2S$ in serum or HeLa cells by the inhibition and displacement of surface plasmon resonance signals, or the act as electrochemical sensors. However, in those methods, the nanosensor is directly mixed with the sample, which will lead to a serious matrix interference. The potential matrix effect of biological samples will result in low selectivity to $H_2S$. Therefore, it is necessary to adopt a new analysis method to eliminate the matrix effect.

Single-drop microextraction (SDME) is a liquid phase microextraction method, which is an efficient analyte extraction method for both liquid and gas analysis. Headspace (HS)-SDME is most effective for volatile compounds. The volatile compounds can be separated from the sample into the headspace, and there is no contact between the solvent and the sample during the extraction. Thus, the problem of interference in complex systems is completely avoided. However, analyzing a single drop is a challenge. In conventional HS-SDME, especially when using microsyringes for analysis, it is generally necessary to analyze the drop in combination with gas or liquid chromatography. Otherwise, it is difficult to use other analysis methods. In recent years, several nanodrop detectors have been developed by many instrument companies for the analysis of extractant drops. However, those detectors are application specific, relatively expensive, and inconvenient to acquire.

SUMMARY

Objective: In order to solve the above technical problems, the present invention provides a method for determining hydrogen sulfide by headspace single-drop liquid phase microextraction and intelligent device colorimetry.

Technical scheme: In order to achieve the above objective, the present invention adopts the following scheme.

A method for determining hydrogen sulfide by headspace single-drop liquid phase microextraction and intelligent device colorimetry, comprising:
  taking a silver-gold core-shell triangular nanosheet (Ag@Au TNS) as a nanodetection probe, in combination with an analysis method of headspace single-drop microextraction (HS-SDME), specifically extracting $H_2S$ volatilized from a sample to be detected by the nanodetection probe, and detecting $H_2S$ in the extracted sample with the help of the photographing function of an intelligent device and a color picking software.
Preferably,
a method for preparing the silver-gold core-shell triangular nanosheet comprises the following steps:
  (1) adding silver nitrate, sodium citrate and hydrogen peroxide to deionized water, stirring the solution, and then quickly adding $NaBH_4$ with the stirring stopped, centrifuging the mixture after a certain period of time, and washing the residue to obtain a silver triangular nanosheet (Ag TNS) for later use;
  (2) re-dispersing the Ag TNS in deionized water, adding PVP and ascorbic acid, and then sequentially adding a silver nitrate solution, a sodium citrate solution and a mixed solution of silver nitrate and sodium citrate dropwise, mixing the mixture well, centrifuging the mixture, and washing the residue with deionized water;
  (3) adding PVP, diethylamine, ascorbic acid and a gold-containing solution to precipitate a gold layer on the surface of the Ag TNS, and finally centrifuging the product, washing the product with deionized water to remove AgNO₃ precipitate and residual PVP to obtain the silver-gold core-shell triangular nanosheet (Ag@Au TNS).

Further preferably, in the step (1), the molar ratio of the silver nitrate to the sodium citrate to the hydrogen peroxide is 1:(10-20):(200-360), and the volume ratio of the mixed solution to NaBH₄ is (1.3-2.5):1.

Further preferably, in the step (2), the PVP, the ascorbic acid, the silver nitrate solution and the sodium citrate solution are used according to the conventional amount.

Further preferably, in the step (3), the volume ratio of the PVP, the diethylamine and the ascorbic acid is (1-9):(0.25-1.25):1, the gold-containing solution comprises PVP, KI, HAuCl₄ and ultrapure water, and the total mass ratio of Ag to Au is (10-4):1.

A method for specifically extracting by the nanodetection probe comprises the following steps:

adding a sample to be detected to a capped container, removing the cap, dropping a trace of Ag@Au TNS solution onto the inner surface of the cap, and then placing the cap on the container, leaving the container standing for a period of time to ensure that H₂S is fully extracted by the extraction drop after being volatilized from the sample, and after the extraction is completed, opening the cap, wherein the drop on the inner surface of the cap is the extracted sample.

A method for detecting H₂S with the help of the photographing function of the intelligent device and the color picking software comprises the following steps:

data measuring: the RGB values are provided directly from the captured image by the color picking software;

standard curve plotting: the calculated difference of the RGB values is taken as the ordinate, and the logarithm of the concentration is taken as the abscissa to obtain a standard curve;

data reading: the limit of detection is calculated from the obtained standard curve according to LOD=3δ black/k, where LOD refers to the limit of detection, δ black is the standard deviation of a blank solution, and k is the slope of the standard curve.

The intelligent device comprises a smartphone and a tablet computer.

The color picking software is EKColorPicker software, a color picker software or ChemEye.

The present invention adopts an intelligent device (such as a smartphone) as a novel analysis device, and provides an interesting platform for diagnosis and environmental monitoring. Based on an intelligent device camera, which is an excellent color imaging sensor, most of the analysis methods developed on the intelligent device are colorimetry and macroscopic feature imaging. By using some color picker software, the color can be analyzed to find the relationship corresponding to the analyzed concentration. In addition, the intelligent device camera is also adapted to take pictures of a single solvent drop, as is present in SDME.

The method of the present invention determines the concentration of H₂S by the ultraviolet-visible (UV-vis) signal inhibition caused by H₂S etching on the pre-added extractant Ag@Au TNS of SDME. The coating of the gold layer not only ensures the high stability of the nanomaterial, but also improves the selectivity of the nanomaterial to H₂S. The HS-SDME method is a simple process that requires only one drop of solvent to complete the analysis.

Beneficial effects: Compared with the prior art, the present invention adopts intelligent device colorimetry, with the limit of detection of about 65 nM and the linear range of 0.1-100 μM, and the established method can be applied to the determination of H₂S in actual samples such as egg white, milk and other opaque samples, and has the advantages of few procedures, simple operation, high detection efficiency and the like.

DESCRIPTION OF THE EMBODIMENTS

Figure 1:
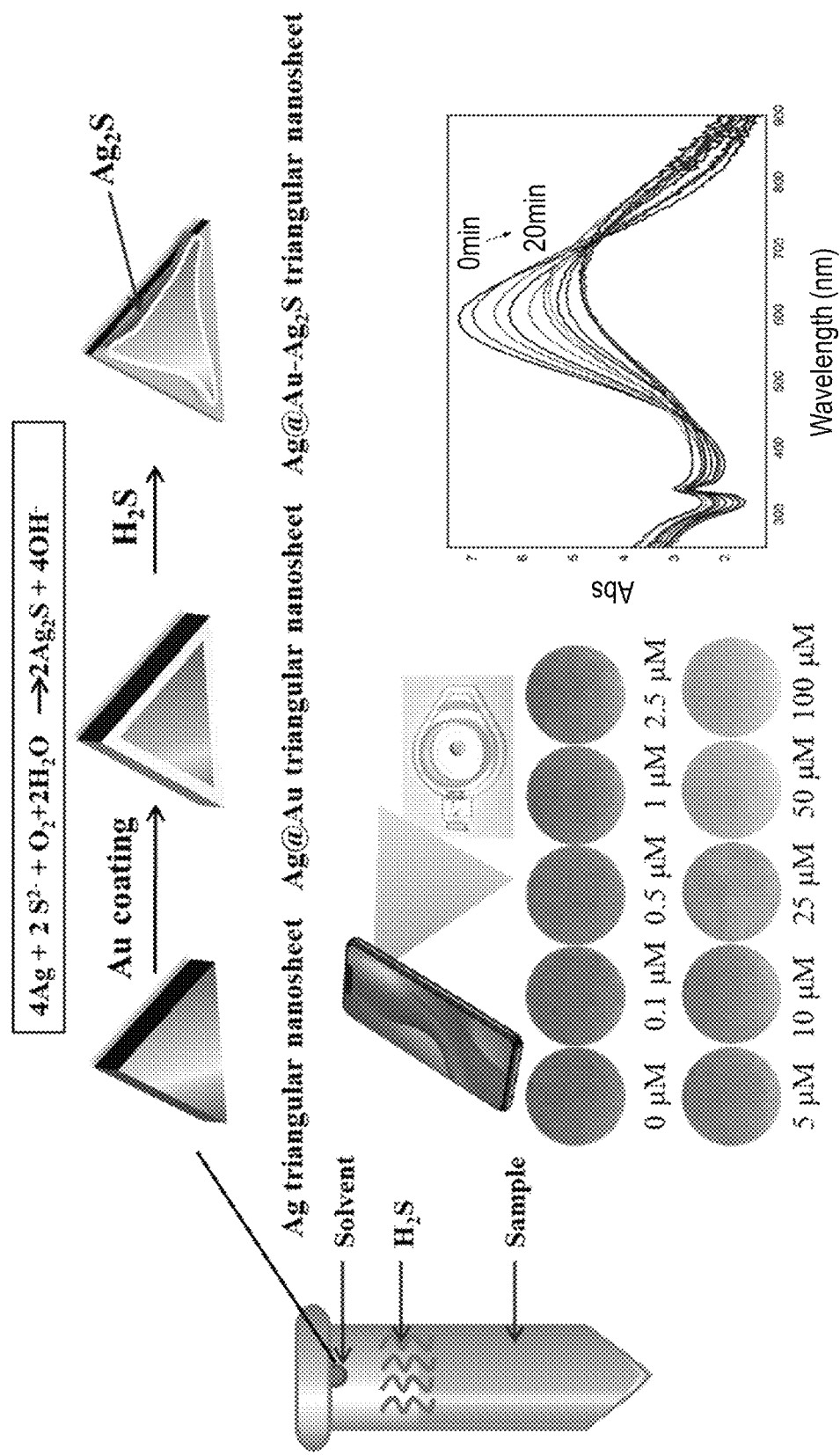
FIG. 1 is a mechanism diagram of a method for detecting H₂S after the headspace single-drop liquid phase microextraction using a silver-gold core-shell triangular nanosheet.

The method of the present invention is further described in detail below with reference to drawings and specific examples.

Example 1. A Method for Determining Hydrogen Sulfide by Headspace Single-Drop Liquid Phase Microextraction and Intelligent Device Colorimetry (1) To a 50 mL beaker were added 40 μL of silver nitrate (0.1 M), 600 μL of sodium citrate (0.1 M), 112 μL of hydrogen peroxide (30%), followed by the addition of deionized water to 39.6 mL. The mixture was stirred rapidly at 30° C. for 10 min using a magnetic stirrer, and then 400 μL of NaBH$_4$ (0.1 M) was rapidly added with the stirring stopped, at which time a pale yellow solution was formed. After 1-2 min, the solution gradually changed from yellow to red, green and then blue, indicating that the preparation of Ag TNS was completed. The solution was centrifuged, and the residue was washed 3 times with deionized water, and stored in the dark at 4° C. before use.

Figure 2:
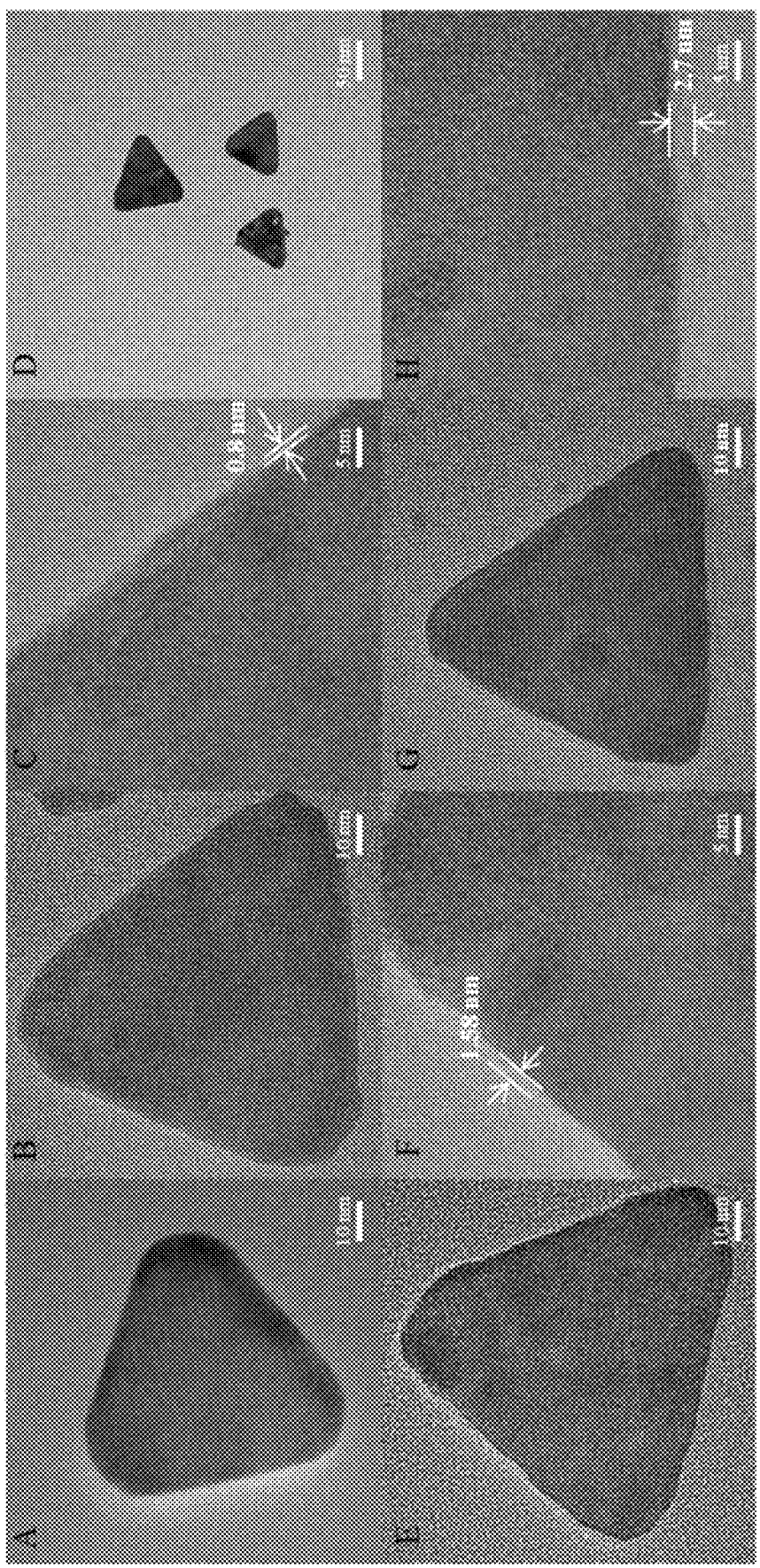
FIG. 2 shows TEM images of the prepared Ag TNS and Ag@Au TNS with three different thicknesses of gold layers: I (B and C), II (D, E and F), III (G and H); wherein A is a TEM image of Ag TNS; B and C are TEM images of Ag@Au TNS with gold layer I; D, E and F are TEM images of Ag@Au TNS with gold layer II; G and H are TEM images of Ag@Au TNS with gold layer III.

(2) The prepared Ag TNS (20 mL) was washed by centrifugation, re-dispersed in 4.5 mL of deionized water, and grown laterally and vertically by the following steps. 500 μL of PVP (17.5 mM vinyl pyrrole monomer) and 18.7 μL of ascorbic acid (0.5 M) were added to aqueous Ag TNS solution, and 300 μL of silver nitrate (0.6 mM) was added to the Ag TNS solution at 0.1 mL/min using a 1 mL disposable syringe. Then 150 μL of sodium citrate (0.1 M) was added to the Ag TNS solution at 0.1 mL/min using a 1 mL disposable syringe, and after 15 min, 1.5 mL of a mixed solution of silver nitrate and sodium citrate was added to the Ag TNS solution at 0.1 mL/min using a 2 mL disposable syringe. The solution was mixed well without further purification and centrifuged, and the residue was washed with deionized water. Then 500 μL of PVP, 75 μL of diethylamine, 100 mL of ascorbic acid (0.5 M) and 500 μL of gold-containing solution were added to precipitate a gold layer on the Ag TNS surface. Finally, the product (Ag@Au TNS) was centrifuged and washed several times with deionized water at room temperature to remove AgNO$_3$ precipitate and residual PVP. Ag@Au TNS was stored in the dark at 4° C. before use. TEM images of the prepared Ag TNS and Ag@Au TNS with three different thicknesses of gold layers are shown in FIG. 2. It can be seen from FIG. 2A that the average side length of Ag TNS was about 55 nm. The three different thicknesses of Au layers of Ag@Au TNS were 0.8 nm, 1.58 nm, and 2.7 nm, respectively, as shown in FIGS. 2B-2H.

Figure 3:
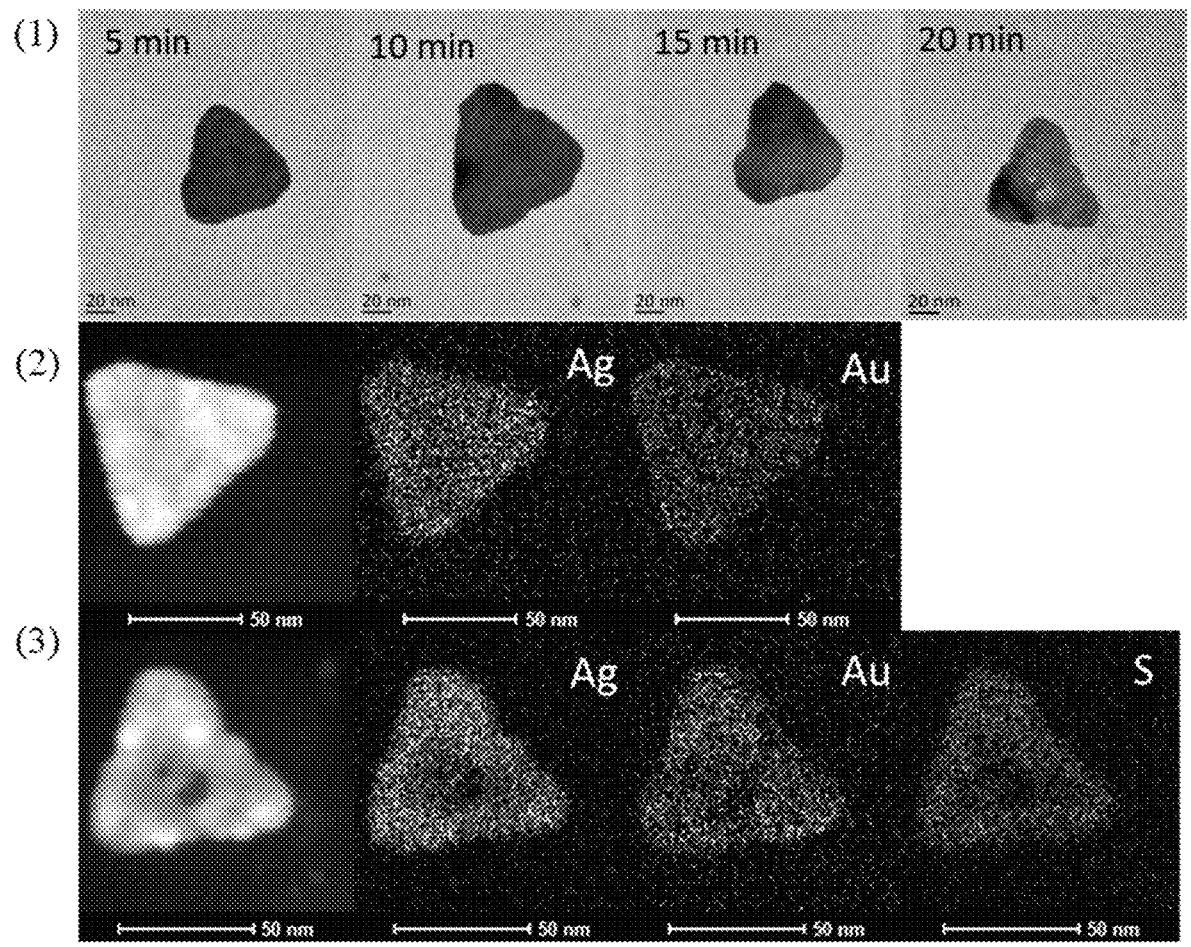
FIG. 3 shows TEM images of Ag@Au TNS incubated in 100 μM H₂S for 5 min, 10 min, 15 min and 20 min, respectively, and EDX mappings before and after the reaction. wherein 1) shows TEM images of Ag@Au TNS incubated in 100 μM H₂S for 5 min, 10 min, 15 min and 20 min, respectively; 2) is an EDX mapping of Ag@Au TNS before the reaction with 100 μM H₂S; 3) is an EDX mapping of Ag@Au TNS after the reaction with 100 μM H₂S.
Figure 4:
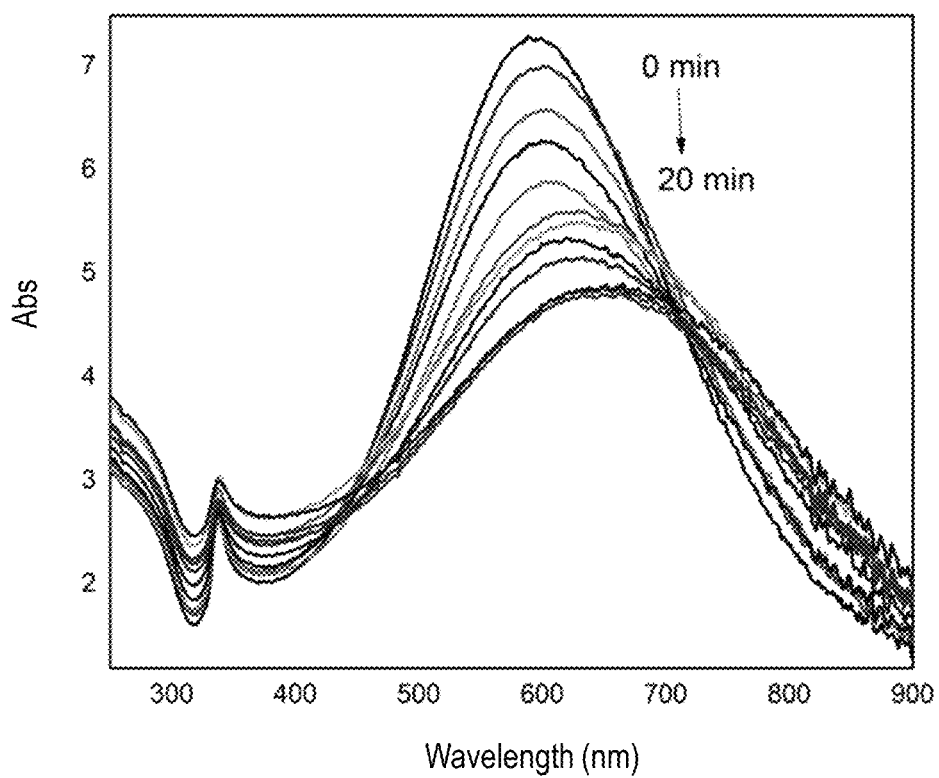
FIG. 4 is a diagram of changes in UV-vis absorption spectrum of Ag@Au TNS by 100 μM H₂S HS-SDME for 20 min.

(3) Sample solutions were prepared, and their aqueous solutions were freshly prepared and stored at 4° C. in the dark due to the instability of Na$_2$S. Fresh milk and eggs were purchased directly from a supermarket without further processing. Each actual sample type was stored in two groups at ambient temperature (25° C.) and 4° C. TEM images of the extraction of H$_2$S by Ag@Au TNS for 5 min, 10 min, 15 min and 20 min, respectively, and EDX mappings of Ag@Au TNS before and after the extraction are shown in FIG. 3. The overall shape of Ag@Au TNS remained unchanged after contact with H$_2$S, although the edges were shrunk and deformed. The EDX results show that there is no significant difference in sulfur distribution between edges and corners.

(4) A mechanism diagram of a method for detecting H$_2$S after the headspace single-drop liquid phase microextraction using a silver-gold core-shell triangular nanosheet is shown in FIG. 1. Firstly, 1.0 mL of Na$_2$S solutions at various concentrations or actual samples were added to a 1.5 mL capped polypropylene centrifuge tube, and then 3.0 μL of the Ag@Au TNS solution was dropped onto the inner surface of the cap. With the help of the surface tension of water and intermolecular forces, the drop does not easily fall from the top unless the centrifuge tube is shaken vigorously. It is therefore feasible to perform SDME in this way. The cap was quickly and gently placed on the centrifuge tube and the tube was left standing for 20 min to ensure that H$_2$S was fully extracted by the extraction drop after being volatilized from the sample. After SDME, the cap of the centrifuge tube was carefully opened and 3.0 μL of the extractant was transferred to a NanoPhotometer UV-vis spectrophotometer using a pipette for analysis of its UV-vis signal. For SNC, a picture of the drop was taken by the smartphone camera. The RGB (red, green, blue) colors of the image were analyzed by EKColorPicker. The R (red) value of the image was provided directly by EKColorPicker software to indicate the intensity of the color.

The addition of PVP, ascorbic acid and sodium citrate needs to be carried out at intervals of 10 min.

In the mixed solution of silver nitrate and sodium citrate, the concentration of silver nitrate was 0.75 mM, and the concentration of sodium citrate was 1.13 mM.

The gold-containing solution comprises 400 μL of PVP (0.5 M vinylpyrrolidone monomer), 80 μL of KI (0.2 M), 20 μL of HAuCl$_4$ (0.25 M) and 3 mL of ultrapure water, and was added at a rate of 0.05 mL/min.

The NaBH$_4$ (0.1 M) was prepared in ice water and prepared freshly just before use.

(5) Data processing

Data measuring: the RGB values were provided directly from the captured image by the color picking software, and a standard curve was plotted by measuring the R (red) values.

Standard curve plotting: the calculated difference of the R values was taken as the ordinate, and the logarithm of the concentration of 0.01-100 μM was taken as the abscissa to obtain a standard curve.

Figure 5:
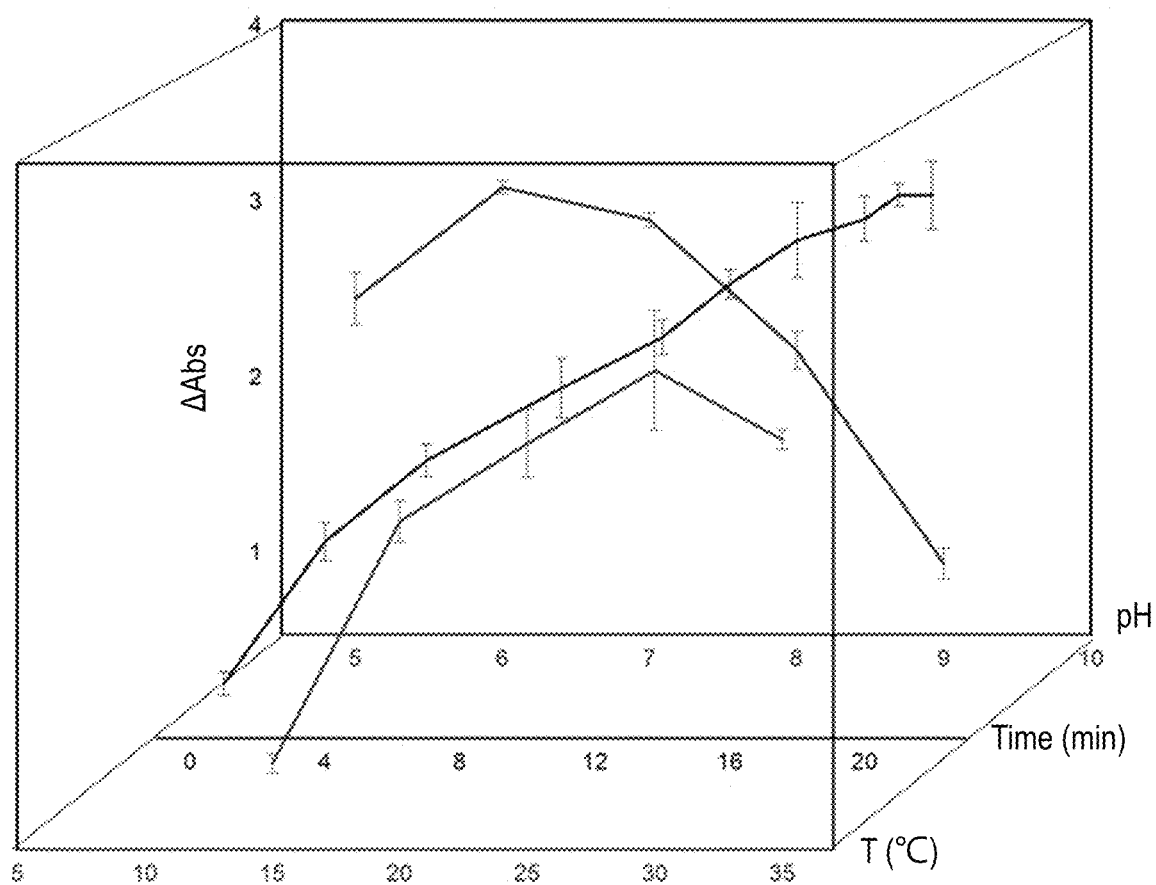
FIG. 5 is an optimization diagram of Ag@Au TNS incubated in 100 μM H₂S at temperatures from 15° C. to 35° C. and pH from 5 to 9 for an incubation time from 0 min to 20 min.
Figure 8:
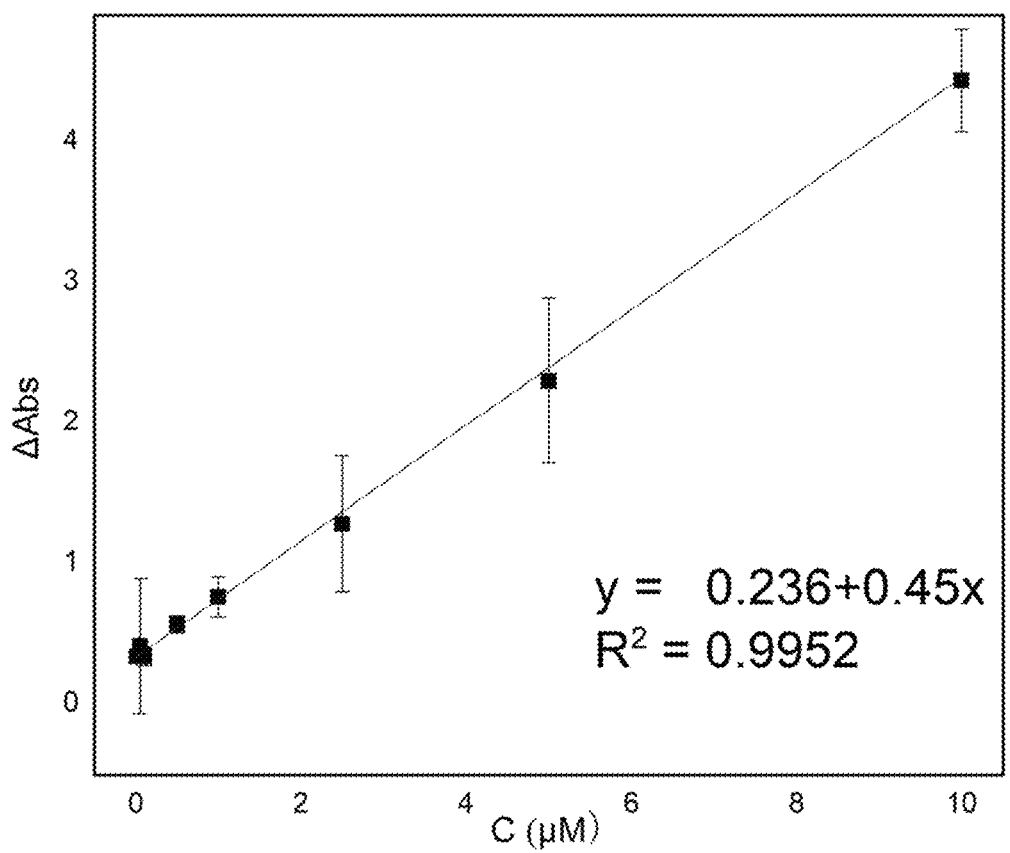
FIG. 8 is a calibration curve of the UV detection of H₂S. Conditions are as follows: incubating in 100 μM H₂S at pH 6 and 30° C. for 20 min.
Figure 9:
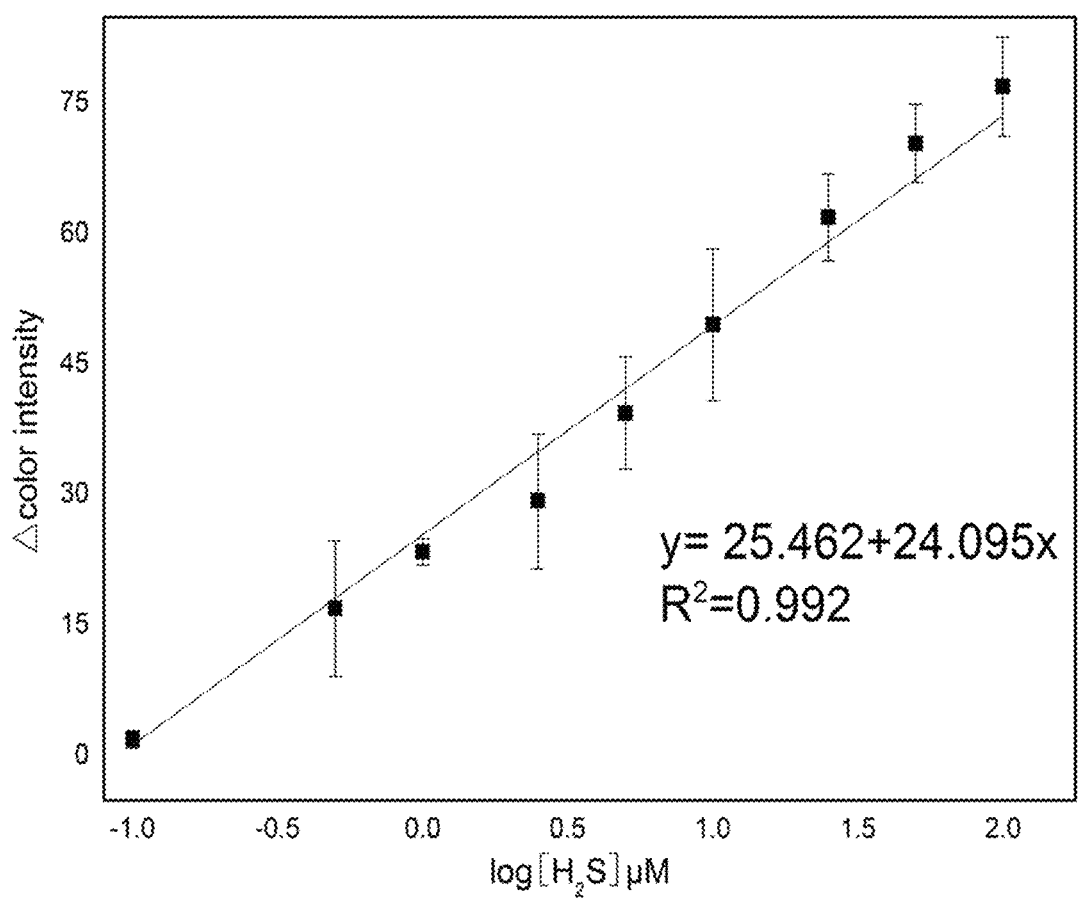
FIG. 9 is a calibration curve of the smartphone nanocolorimetry of H₂S. Conditions are as follows: incubating in 100 μM H₂S at pH 6 and 30° C. for 20 min.

Data reading: the limit of detection was calculated from the obtained standard curve according to LOD=3δ black/k, where LOD refers to the limit of detection, δ black is the standard deviation of unreacted Ag@Au TNS, and k is the slope of the standard curve. FIG. 5 is a diagram of optimization experiments, with the optimal experimental conditions of pH 6, 30° C. and 20 min of the extraction. FIGS. 8 and 9 are calibration curves of the UV detection of H$_2$S and the smartphone nanocolorimetry of H$_2$S, respectively. The LODs are about 7 nM and about 65 nM, respectively, and the linear ranges are 10 nM-10 μM and 0.1 μM-100 μM, respectively.

Figure 10:
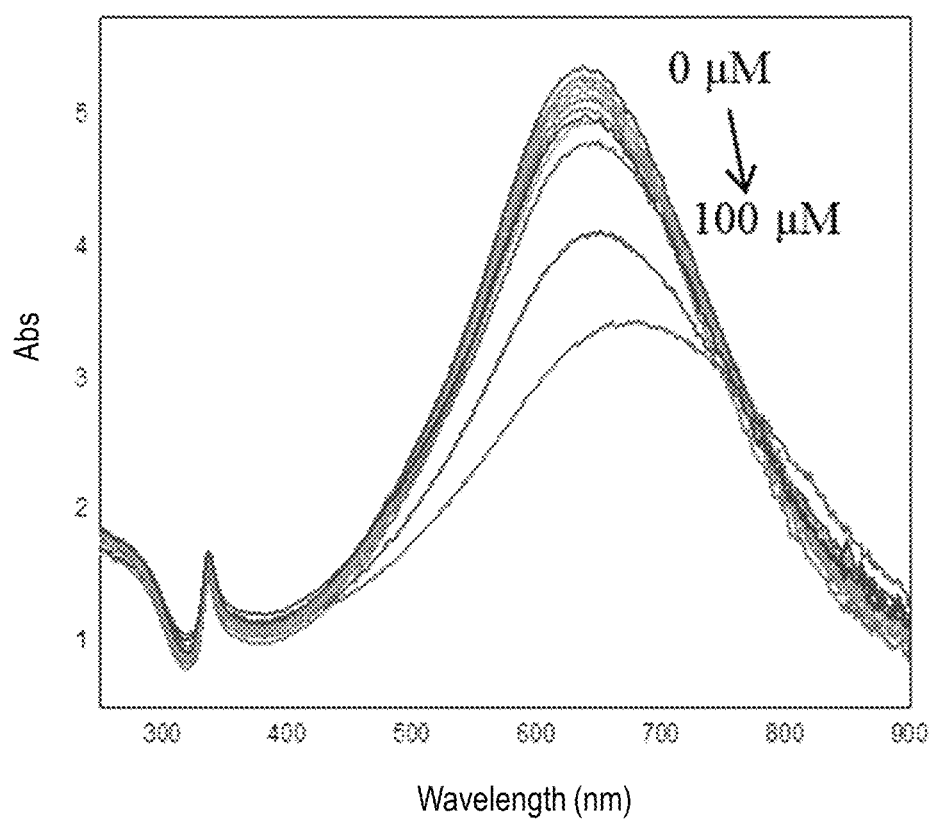
FIG. 10 is a diagram of UV spectra corresponding to H₂S at different concentrations.

FIG. 10 is a diagram of UV spectra corresponding to H$_2$S at different concentrations.

Figure 6:
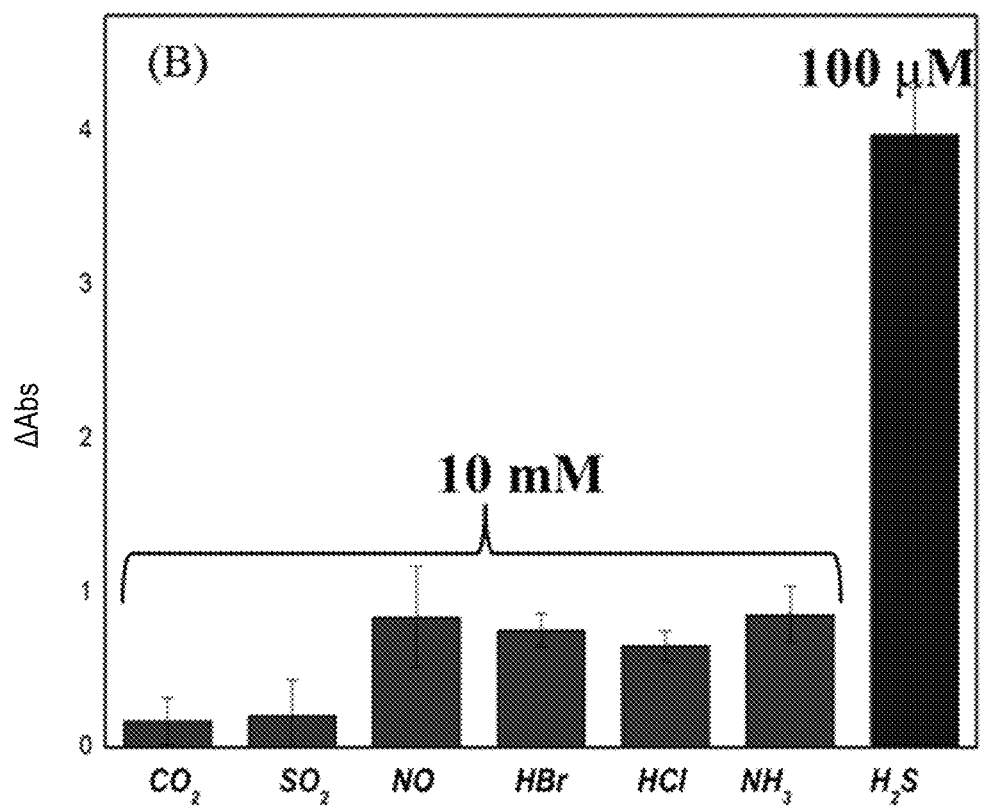
FIG. 6 is a detection diagram of selectivities of Ag@Au TNS in volatile gases such as 10 mM CO2, 10 mM S02, 10 mM NO, 10 mM HBr, 10 mM HCl, 10 mM NH₃ and 100 μM H₂S, respectively.
Figure 7:
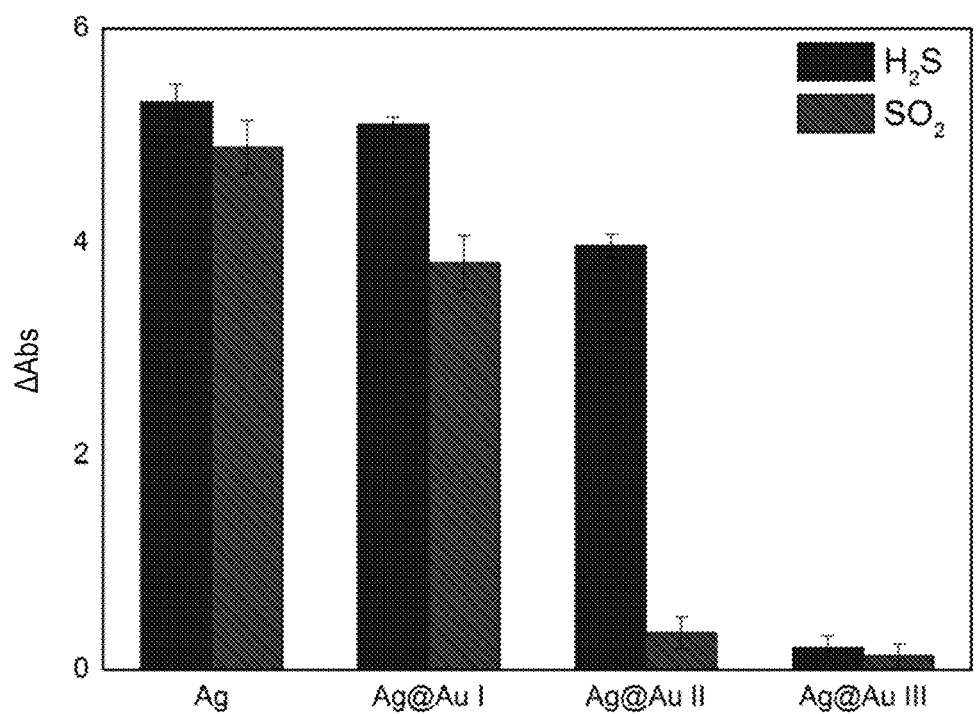
FIG. 7 is a diagram of changes in absorption spectra of Ag TNS and Ag@Au TNS I, II and III in 100 μM Na₂S solution (blue) and 100 μM Na₂SO₃ solution (red) by HS-SDME for 20 min.

To evaluate the selectivity of Ag@Au TNS, 10 mM CO2, 10 mM SO$_2$, 10 mM NO, 10 mM HBr, 10 mM HCl, 10 mM NH$_3$, and 100 μM H$_2$S were extracted for the study, respectively. As shown in FIG. 6, Ag@Au TNS has the best selectivity to H$_2$S. Since the thickness of the Au layer plays a key role in the successful detection of H$_2$S, the effect of this parameter on sensitivity and selectivity was also evaluated. Herein, SO$_2$ was used as interference factor. As shown in FIG. 7, the sensitivity is slightly reduced but the selectivity is enhanced with the increase in the thickness of the Au layer. As shown in FIG. 7, Ag@Au II TNS is the best extractant of the four materials for the extraction under the conditions of H$_2$S and SO$_2$.

Example 2. Detection of H$_2$S in Milk

Figure 11:
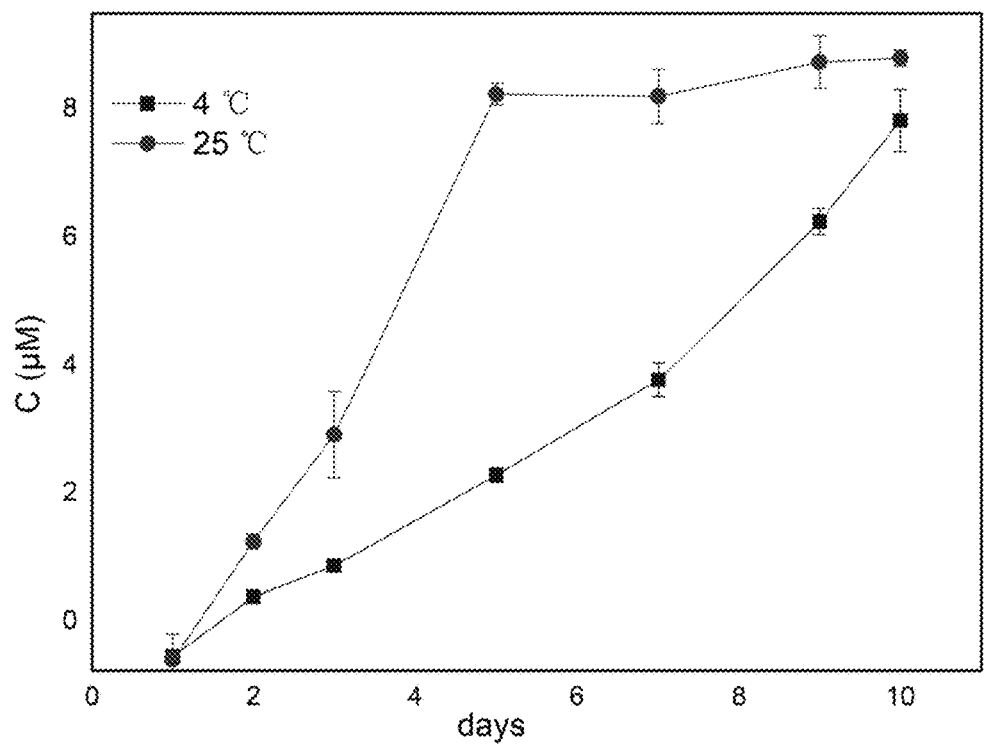
FIG. 11 shows change curves of the concentrations of H₂S in the milk stored at 4° C. and 25° C. over 10 days, respectively.

To detect the trend of H$_2$S content in milk, H$_2$S in fresh milk samples was detected and continuously monitored for 10 days. Fresh milk purchased directly from a supermarket was stored in two beakers, which were kept in a refrigerator at 4° C. and at room temperature (25° C.), respectively. The experimental data were measured using a UV-vis spectrophotometer to obtain a trend diagram of H$_2$S in milk over 10 days, as shown in FIG. 11. To evaluate the matrix effect, the samples were added with 0.02 μM, 0.2 μM and 2 μM H$_2$S, respectively, and detected by a UV-vis spectrophotometer; added with 0.2 μM, 2 μM and 20 μM $H_2S$, respectively, and detected by the smartphone nanocolorimetry. The results are shown in Tables 1 and 2, respectively, and good recovery rates are obtained (97%-105%). In HS-SDME, the matrix interference problem is completely avoided, and the data measuring and calculating are similar to those of the determination of $H_2S$ in aqueous solution.

TABLE 1

Determination of the content of acid labile sulfides added to fresh milk samples by the HS-SDME-UV-vis method

| Sample | Concentration of added sulfide (μM) | Concentration of sulfide (μM) (RSD %, n = 3) | Relative recovery[a] (%) |
|---|---|---|---|
| Milk | — | 1.31 (5) | — |
| | 0.02 | 1.33 (4.5) | 101.10 |
| | 0.2 | 1.52 (3.21) | 104.50 |
| | 2 | 3.32 (6.3) | 100.70 |

[a]Relative recovery = (total concentration − blank concentration)/incorporation concentration

TABLE 2

Determination of the content of acid labile sulfides added to fresh milk samples by the HS-SDME-SNC method

| Sample | Concentration of added sulfide (μM) | Concentration of sulfide (μM) (RSD %, n = 3) | Relative recovery (%) |
|---|---|---|---|
| Milk | — | 0.27 (5.45) | — |
| | 0.2 | 0.46 (1.33) | 97.10 |
| | 2 | 2.22 (3.86) | 97.60 |
| | 20 | 20.0 (1.79) | 99.80 |

Example 3. Detection of $H_2S$ in Eggs

Figure 12:
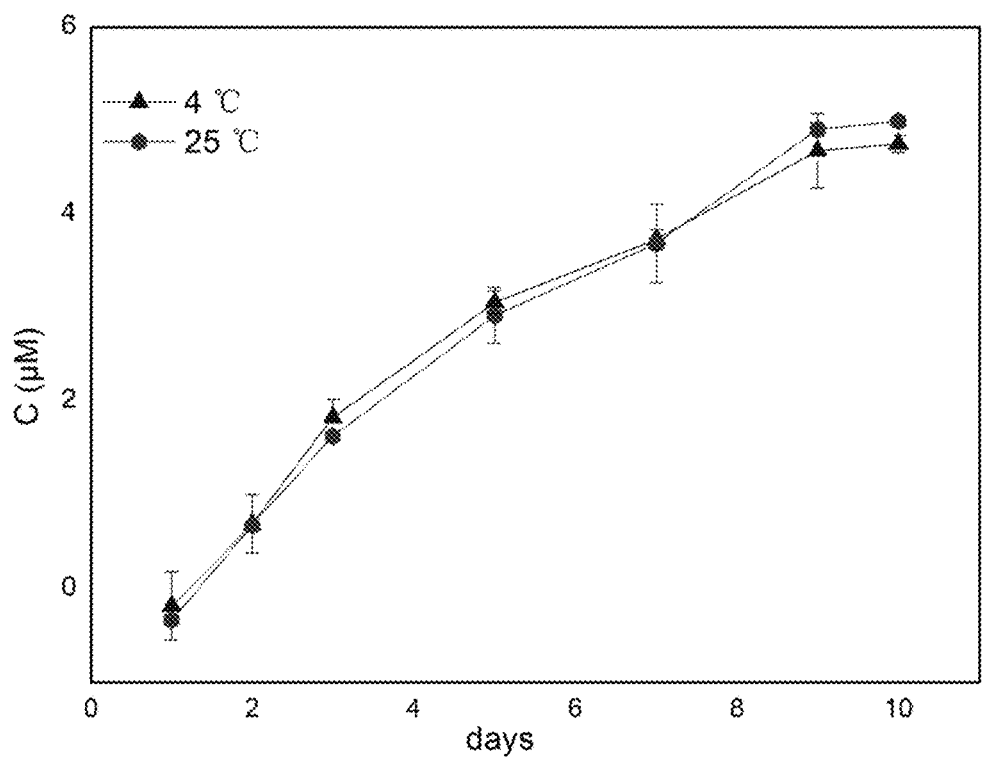
FIG. 12 shows change curves of the concentrations of H₂S in eggs stored at 4° C. and 25° C. over 10 days, respectively.

To detect the trend of $H_2S$ content in eggs, $H_2S$ in egg samples was detected and continuously monitored for 10 days. Eggs purchased directly from a supermarket were stored in a refrigerator at 4° C. and at room temperature (25° C.), respectively. An opening of 5 mm in diameter is made at one end of the egg shell. The experimental data were measured using a UV-vis spectrophotometer to obtain a trend diagram of $H_2S$ in eggs over 10 days, as shown in FIG. 12. To evaluate the matrix effect, the samples were added with 0.02 μM, 0.2 μM and 2 μM $H_2S$, respectively, and detected by a UV-vis spectrophotometer; added with 0.2 μM, 2 μM and 20 μM $H_2S$, respectively, and detected by the smartphone nanocolorimetry. The results are shown in Tables 3 and 4, respectively, and good recovery rates are obtained (95%-104%).

TABLE 3

Determination of the content of acid labile sulfides added to egg samples by the HS-SDME-UV-vis method

| Sample | Concentration of added sulfide (μM) | Concentration of sulfide (μM) (RSD %, n = 3) | Relative recovery (%) |
|---|---|---|---|
| Egg | — | 3.61 (2.62) | — |
| | 0.02 | 3.62 (5.4) | 95.20 |
| | 0.2 | 3.81 (2.17) | 104.00 |
| | 2 | 5.61 (3.9) | 100.13 |

TABLE 4

Determination of the content of acid labile sulfides added to egg samples by the HS-SDME-SNC method

| Sample | Concentration of added sulfide (μM) | Concentration of sulfide (μM) (RSD %, n = 3) | Relative recovery (%) |
|---|---|---|---|
| Egg | — | 2.15 (6.2) | — |
| | 0.2 | 2.35 (5.3) | 100.20 |
| | 2 | 4.19 (1.82) | 102.32 |
| | 20 | 21.8 (1.6) | 98.34 |

What is claimed is:

1. A method for determining hydrogen sulfide ($H_2S$) by headspace single-drop liquid phase microextraction and intelligent device colorimetry, comprising: taking a silver-gold core-shell triangular nanosheet (Ag@Au TNS) as a nanodetection probe, in combination with an analysis method of headspace single-drop microextraction (HS-SDME), specifically extracting $H_2S$ volatilized from a sample to be detected by the nanodetection probe, and detecting $H_2S$ in the extracted sample with the help of the photographing function of an intelligent device and a color picking software.

2. The method according to claim 1, wherein a method for preparing the silver-gold core-shell triangular nanosheet comprises the following steps: step (1) adding silver nitrate, sodium citrate and hydrogen peroxide to deionized water, stirring the solution, and then quickly adding $NaBH_4$ with the stirring stopped, centrifuging the mixture after a certain period of time, and washing the residue to obtain a silver triangular nanosheet (Ag TNS) for later use; step (2) re-dispersing the Ag TNS in deionized water, adding PVP and ascorbic acid, and then sequentially adding a silver nitrate solution, a sodium citrate solution and a mixed solution of silver nitrate and sodium citrate dropwise, mixing the mixture well, centrifuging the mixture, and washing the residue with deionized water; and step (3) adding PVP, diethylamine, ascorbic acid and an aqueous gold-containing solution to precipitate a gold layer on the surface of the Ag TNS, and finally centrifuging the product, washing the product with deionized water to remove $AgNO_3$ precipitate and residual PVP to obtain the silver-gold core-shell triangular nanosheet (Ag@Au TNS).

3. The method according to claim 2, wherein in the step (1), the molar ratio of the silver nitrate to the sodium citrate to the hydrogen peroxide is 1:(10-20):(200-360), and the volume ratio of the mixed solution to $NaBH_4$ is (1.3-2.5):1.

4. The method according to claim 2, wherein in the step (3), the volume ratio of the PVP, the diethylamine and the ascorbic acid is (1-9):(0.25-1.25):1, the aqueous gold-containing solution comprises PVP, KI, $HAuCl_4$ and ultrapure water, and the total mass ratio of Ag to Au is (10-4):1.

5. The method according to claim 1, wherein a method for specifically extracting by the nanodetection probe comprises the following steps: adding a sample to be detected to a container having a cap, removing the cap, dropping a trace of Ag@Au TNS solution onto the inner surface of the cap, and then placing the cap on the container, leaving the container standing for a period of time to ensure that $H_2S$ is fully extracted by the extraction drop after being volatilized from the sample, and after the extraction is completed, opening the cap, wherein the drop on the inner surface of the cap is the extracted sample.

6. The method according to claim 1, wherein a method for detecting $H_2S$ with the help of the photographing function of the intelligent device and the color picking software comprises the following steps: data measuring: the RGB values are provided directly from the captured image by the color picking software; standard curve plotting: the calculated difference of the R values is taken as the ordinate, and the logarithm of the concentration is taken as the abscissa to obtain a standard curve; and data reading: the limit of detection is obtained from the obtained standard curve according to LOD=3δ black/k, where LOD refers to the limit of detection, δ black is the standard deviation of a blank solution, and k is the slope of the standard curve.

7. The method according to claim 1, wherein the intelligent device comprises a smartphone or a tablet computer.

8. The method according to claim 1, wherein the color picking software is EKColorPicker software, a color picker software or ChemEye.

\* \* \* \* \*